United States Patent
Righettini

(10) Patent No.: US 6,180,813 B1
(45) Date of Patent: Jan. 30, 2001

(54) BENZYLIDENECYANOACETATES AND A METHOD FOR MAKING BENZYLIDENECYANOACETATES

(75) Inventor: Robin F. Righettini, Apex, NC (US)

(73) Assignee: Lord Corporation, Cary, NC (US)

(*) Notice: Under 35 U.S.C. 154(b), the term of this patent shall be extended for 0 days.

(21) Appl. No.: 09/330,723

(22) Filed: Jun. 11, 1999

(51) Int. Cl.$^7$ .................................................. C07C 255/03
(52) U.S. Cl. ............................................................ 558/400
(58) Field of Search ............................................. 558/400

(56) References Cited

U.S. PATENT DOCUMENTS

| 2,981,650 | 4/1961 | Bäder et al. | 154/129 |
| 5,830,441 | * 11/1998 | Wang et al. | 424/59 |

OTHER PUBLICATIONS

"Bond–Forming Initiation in Spontaneous Addition and Polymerization Reactions Of Alkenes". H.K. Hall, Jr. *Angewandte Chemie*.vol. 22, No. 6 Jun. 1983.

"Novel Copolymers of Trisubstituted Ethylenes with Styrene. II. Halogen Ring–Substituted Methyl 2–Cyano–3–Phenyl–2–Propenoates" Gregory B. Kharas, et al. *Macromolecular Reports* A32(Suppl. 4), 405–414 (1995).

"New Copolymers of Styrene with Some with Some Trisubstituted Ethylenes" G.B. Kharas and C.B. Feinberg. *Polymer Preprints*.29(1), 180 (1988).

"New Copolymers from Electrophilic Trisubstituted Ethylenes and Electron–rich Vinyl Comonomers" H.K. Hall and R.F. Righettini. *Polymer Bulletin* 16, 405–409 (1986).

"Synthesis and Copolymerization of New Trisubstituted Ethylenes" G.B. Kharas and C.J. Petit. *Polymer Preprints* 30(1), 257 (1989).

"Effect of Substituents on the Radical Copolymerization of Ring–Substituted Methyl 2–Cyano–3 Phenyl–2–Propenoates with Styrene" Gregory B. Kharas, et al. *J.M.S. —Pure Appl. Chem*,A34(4), pp. 627–640 (1997).

"Copolymerization of Styrene. IV. Copolymerization with Esters of Benzylidenecyanoacetic Acid" Arie Gilath, et al. *Journal of Applied Polymer Science*.vol. 14, pp. 1491–1505 (1970).

* cited by examiner

Primary Examiner—Floyd D. Higel
Assistant Examiner—Ebenezer Sackey
(74) Attorney, Agent, or Firm—Wayne W. Rupert

(57) ABSTRACT

Benzylidenecyanoacetates having a structure represented by

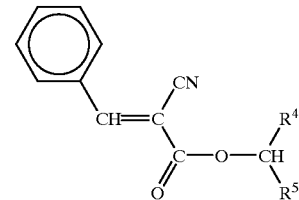

wherein each $R^4$ and $R^5$ is the same or different and is selected from alkoxy, alkyl or alkyl ether. These benzylidenecyanoacetates are liquid at room temperature, have low volatility and are odor free and, thus, are useful in formulating adhesives and coatings.

There is also provided a method for making a benzylidenecyanoacetate having a structure represented by formula B

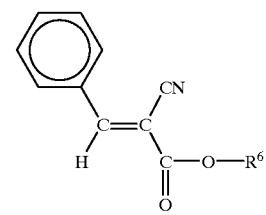

the method including:
  (e) reacting an alkyl cyanoacetate with a benzaldehyde to produce an alkyl benzylidenecyanoacetate and then
  (f) reacting the resulting alkyl benzylidenecyanoacetate with a hydroxy-functional reactant to produce the benzylidenecyanoacetate of formula B,
wherein $R^6$ is an alkyl, alkoxy, alkyl ether or a polymer backbone residue moiety.

8 Claims, No Drawings

BENZYLIDENECYANOACETATES AND A METHOD FOR MAKING BENZYLIDENECYANOACETATES

BACKGROUND OF THE INVENTION

The present invention relates to novel benzylidenecyanoacetate compounds and a novel method for making benzylidenecyanoacetates.

Various benzylidenecyanoacetate compounds have been described in the literature such as ethyl benzylidenecyanoacetate, methyl benzylidenecyanoacetate, n-butyl benzylidenecyanoacetate, n-hexyl benzylidenecyanoacetate, cyclohexyl benzylidenecyanoacetate, 2-ethylhexyl benzylidenecyanoacetate and benzyl ester benzylidenecyanoacetate (see Gilath et al, *J. Appl. Poly Sci.*, 14, 1491 (1970)). However, all of the described benzylidenecyanoacetates are solid at room temperature limiting their usefulness in liquid compositions. It is noted that 2-ethylhexyl benzylidenecyanoacetate has a reported melting point of 27.5° C., but the phase change within a typical room temperature range of 20–30° C. also causes difficulty in using 2-ethylhexyl benzylidenecyanoacetate in liquid compositions. A need exists for benzylidenecyanoacetates that are liquid throughout typical room temperature ranges.

A need also exists for a synthetic method for benzylidenecyanoacetates that is more amenable to larger scale production.

SUMMARY OF THE INVENTION

According to the present invention there are provided novel benzylidenecyanoacetate compounds having a generic structure represented by formula A below.

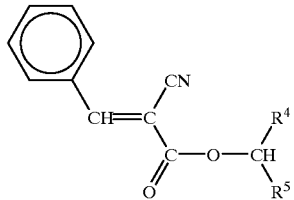

wherein each $R^4$ and $R^5$ is the same or different and is selected from alkoxy, alkyl or alkyl ether. These benzylidenecyanoacetates are referred to herein as "secondary" benzylidenecyanoacetates since the carbon atom bonded to —OOC— is also bonded to two non-hydrogen atoms (meaning that it is bonded to only one hydrogen atom).

The secondary benzylidenecyanoacetates of the invention are useful to form the basis of liquid reactive, two-part adhesives because they have low volatility and are odor free. In addition, due to the presence of only one ester group the benzylidenecyanoacetates of the invention can be the precursor to a wide range of derivative such as capped oligomers useful as toughening agent components in multi-component compositions.

There is also provided a method for making a benzylidenecyanoacetate having a structure represented by formula B

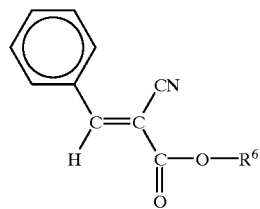

the method comprising:
(a) reacting an alkyl cyanoacetate with a benzaldehyde to produce an alkyl benzylidenecyanoacetate and then
(b) reacting the resulting alkyl benzylidenecyanoacetate with a hydroxy-functional reactant to produce the benzylidenecyanoacetate of formula B, wherein $R^6$ is an alkyl, alkoxy, alkyl ether or a polymer backbone residue moiety. This method is more amenable to larger scale production.

DETAILED DESCRIPTION OF THE PREFERRED EMBODIMENTS

Unless otherwise indicated, description of components in chemical nomenclature refers to the components at the time of addition to any combination specified in the description, but does not necessarily preclude chemical interactions among the components of a mixture once mixed.

As used herein, the following terms have certain meanings.

"Room temperature" means ambient workplace (manufacturing or assembly plant, laboratory, etc.) temperature range, typically 10–40° C., more typically 20–30° C.

Preferably, $R^4$ and $R^5$ of formula A are different and each have 1 to 10 carbon atoms and more preferably are methyl, ethyl, propyl, methoxy, hexyl, ethoxy, butyl, pentyl and branched alkyl groups. Benzylidenecyanoacetates are identified herein according to the —CH($R^4$)($R^5$) structure. For example, if $R^4$ is a methyl group and $R^5$ is a hexyl group then the —CH($R^4$)($R^5$) structure as a whole is a 2-octyl group and the benzylidenecyanoacetate is referred to as "2-octyl benzylidenecyanoacetate".

Certain secondary benzylidenecyanoacetates such as ±1-methoxy-2-propyl benzylidenecyanoacetate and ±2-octyl benzylidenecyanoacetate are particularly useful because it has been found that they exist as liquids at room temperature. It should be recognized that these are racemic mixtures of a chiral compound. Racemic mixtures are preferred over the pure stereoisomers since the pure stereoisomers would be more prone to crystallization.

The benzylidenecyanoacetates of formula A of the invention can be made by two alternative methods. One of these methods is an embodiment of the method of the invention for making benzylidenecyanoacetates of formula B.

According to one method, the acid chloride of cyanoacetic acid is prepared by reacting the cyanoacetic acid with phosphorus pentachloride. Then the acid chloride is reacted with an alcohol having the desired —CH($R^4$)($R^5$) structure to produce an alkyl cyanoacetate. Finally, the alkyl cyanoacetate and a benzaldehyde are subjected to catalyzed Knoevenagel condensation to produce the desired benzylidenecyanoacetate of the invention.

According to a second method, methyl cyanoacetate and benzaldehyde first are subjected to catalyzed Knoevenagel condensation to produce methyl benzylidenecyanoacetate. The methyl benzylidenecyanoacetate then is transesterified with an alcohol having the desired —CH(R⁴)(R⁵) structure to produce the desired benzylidenecyanoacetate of the invention. This second method is an embodiment of the method of the invention for making benzylidenecyanoacetates of formula B.

As described above, the method according to the invention for making benzylidenecyanoacetates of formula B includes two steps. The first step (a) typically involves subjecting an alkyl cyanoacetate and benzaldehyde to catalyzed Knoevenagel condensation. The alkyl group of the alkyl cyanoacetate can be any straight chain or branched alkyl such as methyl, ethyl, n-propyl, isopropyl and butyl or a an alkyl substituted with a functional group such as 2-phenyl ethyl. The resulting product is an alkyl benzylidenecyanoacetate wherein the alkyl group is the same as the alkyl group of the alkyl cyanoacetate.

The catalyzed Knoevenagel condensation of aldehydes with cyanoacetates is generally described in Gilath et al, *J. Appl. Poly Sci.*, 14, 1491 (1970). This condensation reaction typically is performed in a conventional solvent such as hexane, cyclohexane, heptane, octane, benzene, toluene, xylene, ethanol and propanol. The catalyst usually is a base capable of removing a proton from the cyanoacetate. Examples include piperidine, mixture of piperidine with acetic acid, pyridine, diethyl amine, propyl amine, potassium hydroxide, triethyl amine and butyl lithium. The reaction temperature typically is controlled by the boiling point of the solvent. Water is evolved in this reaction, and it may or may not be removed by distillation. The exotherm, if any, can be controlled by the slow addition of one of the reactants. The amount of benzaldehyde and alkyl cyanoacetate reactants can vary, but a substantially 1:1 mole ratio is preferred.

The second step (b) typically involves transesterifying a hydroxy-functional material with the alkyl benzylidenecyanoacetate produced in step (b). The hydroxy-functional material can be an alcohol such as monohydric alcohol or polyhydric alcohol such as a diol or triol, preferably an alkyl alcohol. The hydroxy-functional material also could be a hydroxy-functional polymer or oligomer as described in concurrently filed, commonly-assigned U.S. Patent Application titled "Trifunctional Olefinic-Capped Polymers and Compositions That Include Such Polymers" (Attorney Docket No. IR-2377C(EC)). Examples of hydroxy-functional polymers include hydroxy-terminated polymers such as polyether polyols, hydroxy-terminated dienes, hydroxy-terminated silicones and hydroxy-terminated polyesters and hydroxy-side chain polymers such as polymers and copolymers of 2-hydroxy (meth)acrylate, poly(vinyl alcohol), poly(vinyl acetals), poly(vinyl phenol), cellulose, chitin and oligomerized castor oil. Illustrative polyether polyols include ethylene oxide-capped poly(propylene oxide), poly(tetramethylene glycol) and other hydroxy-terminated oligomers and polymers of ethylene oxide, propylene oxide and tetrahydrofuran. Illustrative hydroxy-terminated dienes include hydroxy-terminated polybutadiene, hydroxy-terminated poly(butadiene-acrylonitrile) and hydroxy-terminated poly(butadiene-methacrylonitrile-acrylic acid). In the case of a hydroxy-functional polymer/oligomer reactant, R⁶ will be the backbone structure of the polymer. In other words, it will be the residue structure derived from the reaction of the polymer/oligomer.

Transesterification is a well-known synthesis technique. Catalysts typically are employed such as alkali metal hydroxides such as potassium or sodium hydroxide; lower alkoxides such as potassium methoxide, aluminum isopropoxide and titanium butoxide; imidazole and other organic bases; acids such as sulfuric, hydrochloric and p-toluenesulfonic; oxides, carbonates and acetates of zinc, calcium, magnesium and cobalt; and tin compounds such as dibutyl tin oxide and dibutyl tin dilaurate. The reaction can be done either neat or in the presence of a solvent such as hexane, cyclohexane, heptane, octane, benzene, toluene, and xylene. Typical temperatures for the transesterification range from room temperature to over 200° C., preferably 90 to 200° C., more preferably 110 to 140° C. The reactant amounts of benzylidenecyanoacetate and hydroxy-functional material can vary, but it is preferably 0.05 to 1.10, more preferably 0.85 to 1.00, mole ratio of benzylidenecyanoacetate to hydroxy groups of the hydroxy-functional material.

Free radical copolymerization of the novel benzylidenecyanoacetates with olefinic monomers such as styrenic monomers can be the basis for formulating adhesive and coating compositions as described in commonly-assigned and concurrently filed U.S. Patent Application titled "Reactive Adhesives and Coatings With Trifunctional Olefinic Monomers" (Attorney Docket No. IR-2377A(EC)). The novel benzylidenecyanoacetates also can be useful capping agents for certain oligomers and polymers as described in commonly-assigned and concurrently filed U.S. Patent Application titled "Trifunctional Olefinic-Capped Polymers and Compositions That Include Such Polymers" (Attorney Docket No. IR-2377C(EC)).

The invention is described in more detail by way of the following non-limiting examples.

EXAMPLE 1

Synthesis of ±2-octyl benzylidenecyanoacetate 143.60 g 2-octanol, 206.40 g methyl benzylidenecyanoacetate, 211.70 g cyclohexane and 0.56 g titanium (IV) tetrabutoxide were charged to a flask fitted with an oil bath for heating. The oil bath was heated to 130° C. and methanol was removed as an azeotrope for a period of approximately 25 hours. The methyl benzylidenecyanoacetate used in this synthesis was made by mixing 1.198 kg benzaldehyde, 1.119 kg methyl cyanoacetate, 0.920 kg absolute ethanol and 0.66 g piperidine. The mixture is refluxed for two hours and allowed to cool. The resulting product was a mobile liquid that was ±2-octyl benzylidenecyanoacetate having a representative structure shown below.

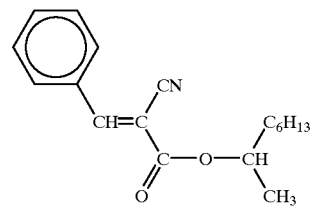

EXAMPLE 2

Synthesis of ±1-methoxy-2-propyl Benzylidenecyanoacetate

A mixture of 27.04 g 1-methoxy-2-propyl cyanoacetate, 18.26 g benzaldehyde, 18.26 g absolute alcohol and 0.0165 piperidine was heated for 22 hours. Additional portions of piperidine were added as needed. The resulting product was a mobile liquid that was ±1-methoxy-2-propyl benzylidenecyanoacetate has a representative structure as shown below.

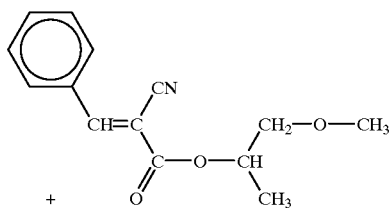

EXAMPLE 3

Synthesis of ±1-ethoxy-2-propyl benzylidenecyanoacetate

A mixture of 93.62 g methyl benzylidenecyanoaceate, 52.19 g 1-ethoxy-2-propanol and 0.5 cc titanium(IV) butoxide was heated in a 140° C. oil bath for 13 hours. Additional charges of 0.2 cc titanium(IV) butoxide was added when the evolution of methanol slowed. The resulting product was a mobile liquid ±1-ethoxy-2-propyl benzylidenecyanoacetate.

What is claimed is:

1. A benzylidenecyanoacetate having a structure represented by:

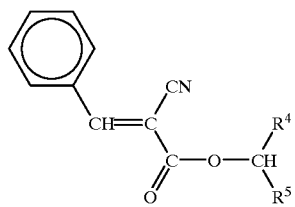

wherein each $R^4$ and $R^5$ is the same or different and is selected from alkoxy, alkyl or alkyl ether.

2. A benzylidenecyanoacetate according to claim 1 wherein $R^4$ and $R^5$ each have 1 to 10 carbon atoms.

3. A benzylidenecyanoacetate according to claim 1 wherein $R^4$ and $R^5$ are selected from methyl, ethyl, propyl, methoxy, hexyl, ethoxy, pentyl and branched alkyl groups.

4. A benzylidenecyanoacetate according to claim 1 wherein $R^4$ and $R^5$ are each different groups.

5. A benzylidenecyanoacetate according to claim 3 wherein $R^4$ and $R^5$ are each different groups.

6. A benzylidenecyanoacetate according to claim 1 that is a liquid at room temperature.

7. A benzylidenecyanoacetate having a structure represented by:

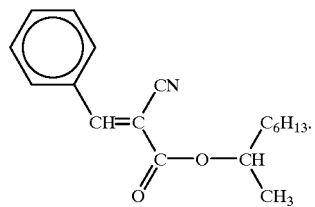

8. A benzylidenecyanoacetate having a structure represented by:

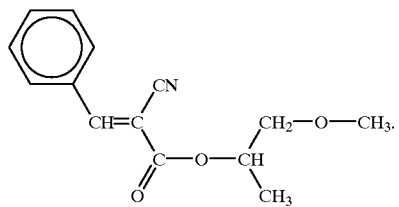

* * * * *